United States Patent [19]

Newbold et al.

[11] Patent Number: 5,411,946
[45] Date of Patent: May 2, 1995

[54] AVERMECTIN DERIVATIVES

[75] Inventors: Ronald C. Newbold, Bound Brook; Thomas L. Shih, Edison, both of N.J.

[73] Assignee: Merck & Co., Inc., Rahway, N.J.

[21] Appl. No.: 21,450

[22] Filed: Feb. 24, 1993

[51] Int. Cl.⁶ .............. A61K 31/70; C07H 17/04
[52] U.S. Cl. ..................... 514/30; 536/7.1; 549/264; 514/450
[58] Field of Search .......... 536/7.1; 549/264; 514/30, 450

[56] References Cited

U.S. PATENT DOCUMENTS

| | | | |
|---|---|---|---|
| 4,310,519 | 1/1982 | Albers-Schonberg et al. | 514/30 |
| 4,550,160 | 10/1985 | Mrozik | 536/7.1 |
| 4,895,837 | 1/1990 | Mrozik et al. | 514/30 |
| 4,897,383 | 1/1990 | Sinclair | 514/30 |
| 4,906,619 | 3/1990 | Eskola et al. | 514/30 |
| 4,945,105 | 7/1990 | Sato et al. | 514/450 |
| 5,015,630 | 5/1991 | Fisher et al. | 514/30 |
| 5,023,241 | 6/1991 | Linn et al. | 514/30 |
| 5,089,480 | 2/1992 | Gibson et al. | 514/30 |

FOREIGN PATENT DOCUMENTS 0421568  4/1991  European Pat. Off.
0506331  9/1992  European Pat. Off.

*Primary Examiner*—Douglas W. Robinson
*Assistant Examiner*—Elli Peselev
*Attorney, Agent, or Firm*—David L. Rose; Joseph F. DiPrima

[57] ABSTRACT

Avermectin derivatives, wherein the C-17-21-25-dioxaspirane substructure has been modified to include substitutions of heteratomic nucleophilic thiols at the 23,24-α-epoxide. These compounds can be similarly substituted at the 4"-, 5-, 13, and 25-positions. The new C-23 and C-24 substituted avermectin derivatives are potent anthelmintic, insecticidal and acaricidal agents.

4 Claims, No Drawings

AVERMECTIN DERIVATIVES

BACKGROUND AND SUMMARY OF THE INVENTION

The instant invention relates generally to bioactive avermectin $B_{2a}$ derivatives which have been modified in the spiroketal region through nucleophilic addition. It is to be understood that the instant invention encompasses both homogeneous $B_{2a}$ and $B_{2b}$ derivatives, as well as naturally occurring mixture of these derivatives.

The avermectin series of compounds, which are isolated from a fermentation broth, having the following structure:
wherein R is the 4'-(α-L-oleandrosyl)-α-L-oleandrose group of the structure

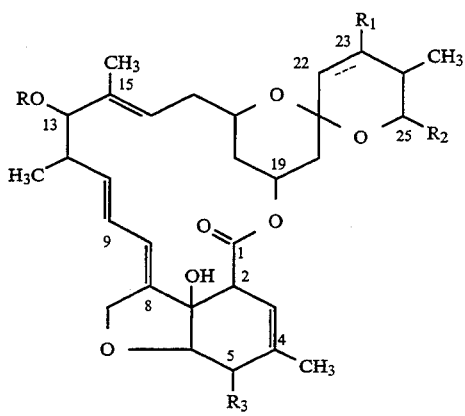

wherein R is the 4'(α-L-oleandrosyl)-α-L oleandrose group of the structure:

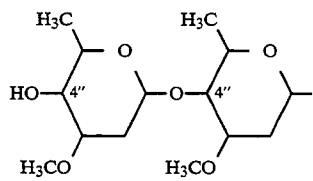

and wherein the broken line indicates a single or a double bond; $R_1$ is hydroxy and is present only when said broken line indicates a single bond;
$R_2$ is iso-propyl or sec-butyl; and
$R_3$ is methoxy or hydroxy.

There are eight different major avermectin natural product compounds and they are given the designations A1a, A1b, A2a, A2b, B1a, B1b, B2a and B2b based upon the structure of the individual compounds.

In the foregoing structural formula, the individual avermectin compounds are as set forth below. (The R group is 4'((α-L-oleandrosyl)-α-oleandrose):

|     | $R_1$              | $R_2$      | $R_3$   |
|-----|--------------------|------------|---------|
| A1a | (22,23-Double Bond)| sec-butyl  | —OCH₃   |
| A1b | (22,23-Double Bond)| iso-propyl | —OCH₃   |
| A2a | —OH                | sec-butyl  | —OCH₃   |
| A2b | —OH                | iso-propyl | —OCH₃   |
| B1a | (22,23-Double Bond)| sec-butyl  | —OH     |
| B1b | (22,23-Double Bond)| iso-propyl | —OH     |
| B2a | —OH                | sec-butyl  | —OH     |
| B2b | —OH                | iso-propyl | —OH     |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

The avermectin class of macrocyclic lactones exhibit unprecedented insecticidal and antiparasitic bioactivities, as disclosed in U.S. Pat. Nos. 4,895,837; 4,550,160; and 4,310,519, the entirety of which are hereby incorporated by reference. Useful modifications of these compounds, however, prove difficult, given avermectins's extreme sensitivity to acidic and basic media employed in traditional chemical techniques.

The instant invention achieves a modification of avermectin to yield a bioactive analog, notwithstanding these synthesis constraints, by a novel substitution at the spiroketal region of the avermectin molecule (C-17-21-25-dioxaspirane substructure) of substituents selected from the group consisting of hydrogen, thioalkyl, thioalkenyl, substituted thioalkyl, thioalkenyl groups, cyano, and heterocyclic nucleophiles derived from a variety of thiols. These avermectin derivatives are prepared by reaction of organometallic reagents with protected avermectin compounds.

Generally, avermectin derivatives of the instant invention are described by the following formulae (III):

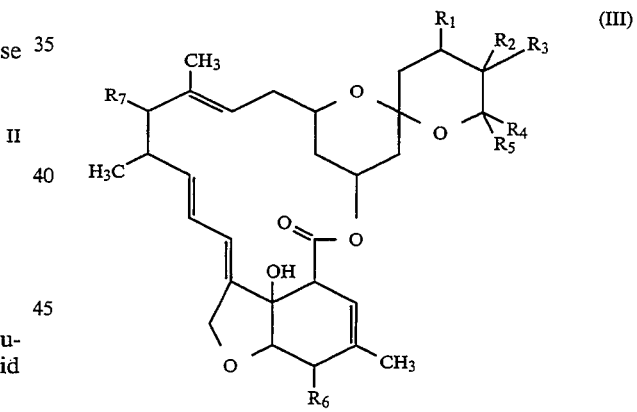

wherein:

$R_1$ is hydrogen, hydroxy, oxo, thiophenyl, thiophenyl substituted with halogen, thiopyridyl, thiothiazolyl, thioimidazolyl, thioacetyl, thioalkyl, and their sulfoxide and sulfone oxidation products;

$R_2$ is hydrogen, hydroxy, thiophenyl, thiophenyl substituted with halogen, cyano, thiopyridyl, thiothiazolyl, thioimidazolyl, thioacetyl, thioalkyl, and their sulfoxide and sulfone oxidation products;

$R_3$ is methyl;

$R_4$ is H or alkyl, alkenyl, branched-alkyl, cycloalkyl;

$R_5$ is H, alkyl, or alkenyl, provided one of $R_4$ or $R_5$ is H;

$R_6$ is OH, oxo, or NOH;

$R_7$ is H, OH, $R_8$-(oleandrosyl)$_n$, (n=1,2,) fluoro, chloro, OCH₂OCH₂CH₂OCH₃,

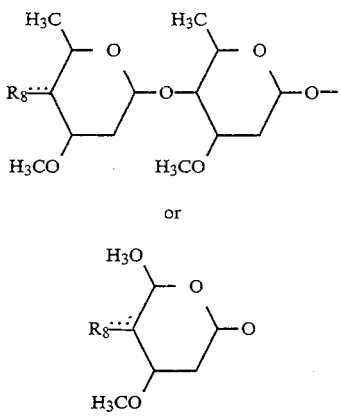

or where $R_8$ is connected to the 4' or 4" carbon atoms by a single bond and is hydroxy, lower alkanoyloxy, lower alkoxy, amino, N-lower alkylamino, N,N-diloweralkylamino, N-loweralkanoylamino, N-lower alkyl-N-lower alkanoylamino, N-lower-alkyl silyloxy or phenoxyloweralkanoyloxy, or $R_8$ is attached to the 4' or 4" carbon atoms by a double bond and is oxo, semicarbazano, N-lower-alkylsemicarbazano, N,N-diloweralkanoylamino, loweralkanoyhydrazono or loweralkylbenzoylhydrazono.

Avermectin derivatives of the instant invention include:

24-(4-fluoro-phenylthio)-avermectin B2a/2b;
4"-epi-acetylamino-4"-deoxy-24-(4-fluoro-thiophenyl)-avermectin B2a/2b;
13-epi-0-acetyl-24-(4-fluoro-thiophenyl)-avermectin B2a/2b aglycone;
13-deoxy-24-(4-fluoro-thiophenyl)-avermectin B2a/2b aglycone;
13-epi-fluoro-13-deoxy-24-(4-fluoro-thiophenyl)-avermectin B2a/2b aglycone;
13-epi-fluoro-13-deoxy-24-(4-fluoro-thiophenyl)-avermectin B2a/2b aglycone-5-oxime;
24-(4-fluoro-thiophenyl)-avermectin B2a/2b-5-oxime;
22,23-dihydro-23-deoxy-23-(4-fluoro-thiophenyl)-24-hydroxy-avermectin B2a/2b.
4"-epi-acetylamino-4"-deoxy-23-deoxy-23-(4-fluorothiophenyl)-24-hydroxy-avermectin B2a/2b;
13-epi-0-acetyl-23-deoxy-23-(4-fluoro-thiophenyl)-24-hydroxy-avermectin B2a/2b aglycone;
13-deoxy-23-deoxy-23-(4-fluoro-thiophenyl)-24-hydroxy-avermectin B2a/2b aglycone;
13-epi-fluoro-13-deoxy-23-deoxy-23-(4-fluorothiophenyl)-24-hydroxy-avermectin B2a/2b aglycone;
13-epi-fluoro-13-deoxy-23-deoxy-23-(4-fluorothiophenyl)-24-hydroxy-avermectin B2a/2b aglycone-5-oxime;
23-deoxy-23-(4-fluoro-thiophenyl)-24-hydroxy-avermectin B2a/2b-5-oxime;
24-(2-thiopyridyl)-avermectin B2a/2b;
4"-epi-acetylamino-4"-deoxy-24-(2-thiopyridyl)-avermectin B2a/2b;
13-epi-0-acetyl-24-(2-thiopyridyl)-avermectin B2a/2b aglycone;
13-deoxy-24-(2-thiopyridyl)-avermectin B2a/2b aglycone
13-epi-fluoro-13-deoxy-24-(2-thiopyridyl)-avermectin B2a/2b aglycone;
13-epi-fluoro-13-deoxy-24-(2-thiopyridyl)-avermectin B2a/2b aglycone-5-oxime;
24-(2-thiopyridyl)-avermectin B2a/2b-5-oxime;
23-deoxy-23-(2-thiopyridyl)-24-hydroxy-avermectin B2a/2b;
4"-epi-acetylamino-4"-deoxy-23-deoxy-23-(2-thiopyridyl)-24-hydroxy-avermectin B2a/2b;
13-epi-0-acetyl-23-deoxy-23-(2-thiopyridyl)-24-hydroxy-avermectin B2a/2b aglycone;
13-deoxy-23-deoxy-23-(2-thiopyridyl)-24-hydroxy-avermectin B2a/2b aglycone;
13-epi-fluoro-13-deoxy-23-deoxy-23-(2-thiopyridyl)-24-hydroxy-avermectin B2a/2b aglycone;
13-epi-fluoro-13-deoxy-23-deoxy-23-(2-thiopyridyl)-24-hydroxy-avermectin B2a/2b aglycone-5-oxime;
23-deoxy-23-(2-thiopyridyl)-24-hydroxy-avermectin B2a/2b-5-oxime;
24-(4-thiopyridyl)-avermectin B2a/2b;
4"-epi-acetylamino-4"-deoxy-24-(4-thiopyridyl)-avermectin B2a/2b;
13-epi-0-acetyl-24-(4-thiopyridyl)-avermectin B2a/2b aglycone;
13-0-methoxy-ethoxy-methyl-24-(4-thiopyridyl)-avermectin B2a/2b aglycone;
4'-0-methoxy-ethoxy-methyl-24-(4-thiopyridyl)-avermectin B2a/2b monosaccharide;
13-deoxy-24-(4-thiopyridyl)-avermectin B2a/2b aglycone;
13-epi-fluoro-13-deoxy-24-(4-thiopyridyl)-avermectin B2a/2b aglycone;
13-epi-fluoro-13-deoxy-24-(4-thiopyridyl)-avermectin B2a/2b aglycone-5-oxime;
24-(4-thiopyridyl)-avermectin B2a/2b-5-oxime;
23-deoxy-23-(4-thiopyridyl)-24-hydroxy-avermectin B2a/2b;
4"-epi-acetylamino-4"-deoxy-23-deoxy-23-(4-thiopyridyl)-24-hydroxy-avermectin B2a/2b;
13-epi-0-acetyl-23-deoxy-23-(4-thiopyridyl)-24-hydroxy-avermectin B2a/2b aglycone;
4'-0-methoxy-ethoxy-methyl-23-(4-thio-pyridyl)-24-hydroxy-24-methyl-avermectin B2a/2b monosaccharide;
13-0-methoxy-ethoxy-methyl-23-deoxy-23-(2-thiopyridyl)-24-hydroxy-avermectin B2a/2b aglycone;
4'-0-methoxy-ethoxy-methyl-22-hydro-23-deoxy-23-(2-thiopyridyl)-24-hydroxy-avermectin B2a/2b monosaccharide;
13-deoxy-23-(4-thiopyridyl)-24-hydroxy-avermectin B2a/2b aglycone;
13-epi-fluoro-13-deoxy-23-deoxy-23-(4-thiopyridyl)-24-hydroxy-24-methyl-avermectin B2a/2b aglycone;
13-epi-fluoro-13-deoxy-23-deoxy-23-(4-thio-pyridyl)-24-hydroxy-avermectin B2a/2b aglycone-5-oxime;
23-deoxy-23-(4-thiopyridyl)-24-hydroxy-avermectin B2a/2b-5-oxime;
24-(2-mercaptothiazolyl)-avermectin B2a/2b;
4"-epi-acetylamino-4"-deoxy-24-(2-mercaptothiazolyl)-avermectin B2a/2b;
13-epi-0-acetyl-24-(2-mercaptothiazolyl)-avermectin B2a/2b aglycone;
13-deoxy-24-(2-mercaptothiazolyl)-avermectin B2a/2b aglycone;
13-epi-fluoro-13-deoxy-24-(2-mercaptothiazolyl)-avermectin B2a/2b aglycone;
13-epi-fluoro-13-deoxy-24-(2-mercaptothiazolyl)-avermectin B2a/2b aglycone-5-oxime;
24-(2-mercaptothiazolyl)-avermectin B2a/2b-5-oxime;
23-deoxy-23-(2-mercaptothiazolyl)-24-hydroxy-avermectin B2a/2b;

4''-epi-acetylamino-4''-deoxy-23-deoxy-23-(2-mercaptothiazolyl)-24-hydroxy-avermectin B2a/2b;

13-epi-0-acetyl-23-deoxy-23-(2-mercaptothiazolyl)-24-hydroxy-avermectin B2a/2b aglycone;

13-deoxy-23-deoxy-23-(2-mercaptothiazolyl)-24-hydroxy-avermectin B2a/2b aglycone;

13-epi-fluoro-13-deoxy-23-deoxy-23-(2-mercaptothiazolyl)-24-hydroxy- 24-avermectin B2a/2b aglycone;

13-epi-fluoro-13-deoxy-23-deoxy-23-(2-mercaptothiazolyl)-24-hydroxy-avermectin B2a/2b aglycone-5-oxime;

23-deoxy-23-(2-mercaptothiazolyl)-24-hydroxy-avermectin B2a/2b-5-oxime;

24-(2-mercaptoimidazolyl)-avermectin B2a/2b

4''-epi-acetylamino-4''-deoxy-24-(2-mercaptoimidazolyl)-avermectin B2a/2b;

13-epi-0-acetyl-24-(2-mercaptoimidazolyl)-avermectin B2a/2b aglycone;

13-deoxy-24-(2-mercaptoimidazolyl)-avermectin B2a/2b aglycone;

13-epi-fluoro-13-deoxy-24-(2-mercaptoimidazolyl)-avermectin B2a/2b aglycone;

13-epi-fluoro-13-deoxy-24-(2-mercaptoimidazolyl)-avermectin B2a/2b aglycone-5-oxime;

24-(2-mercaptoimidazolyl)-avermectin B2a/2b-5-oxime;

23-deoxy-23-(2-mercaptoimidazolyl)-24-hydroxy-avermectin B2a/2b;

4''-epi-acetylamino-4''-deoxy-23-deoxy-23-(2-mercaptoimidazolyl)-24-hydroxy-avermectin B2a/2b;

13-epi-0-acetyl-23-deoxy-23-(2-mercaptoimidazolyl)-24-hydroxy-avermectin B2a/2b aglycone;

13-deoxy-23-deoxy-23-(2-mercaptoimidazolyl)-24-hydroxy-avermectin B2a/2b aglycone;

13-epi-fluoro-13-deoxy-23-deoxy-23-(2-mercaptoimidazolyl)-24-hydroxy-avermectin B2a/2b aglycone 13-epi-fluoro-13-deoxy-23-deoxy-23-(2-mercaptoimidazolyl)-24-hydroxy-avermectin B2a/2b aglycone-5-oxime;

23-deoxy-23-(2-mercaptoimidazolyl)-24-hydroxy-avermectin B2a/2b-5-oxime;

24-thioacetyl-avermectin B2a/2b;

4''-epi-acetylamino-4''-deoxy-24-thioacetyl-avermectin B2a/2b;

13-epi-0-acetyl-24-thioacetyl-avermectin B2a/2b aglycone;

13-deoxy-24-thioacetyl-avermectin B2a/2b aglycone;

13-epi-fluoro-13-deoxy-24-thioacetyl-avermectin B2a/2b aglycone;

13-epi-fluoro-13-deoxy-24-thioacetyl-avermectin B2a/2b aglycone-5-oxime;

24-thioacetyl-avermectin B2a/2b-5-oxime;

23-deoxy-23-thioacetyl-24-hydroxy-avermectin B2a/2b;

4''-epi-acetylamino-4''-deoxy-23-deoxy-23-thioacetyl-24-hydroxy-avermectin B2a/2b;

13-epi-0-acetyl-23-deoxy-23-thioacetyl-24-hydroxy-avermectin B2a/2b aglycone;

13-deoxy-23-deoxy-23-thioacetyl-24-hydroxy-avermectin B2a/2b aglycone;

13-epi-fluoro-13-deoxy-23-deoxy-23-thioacetyl-24-hydroxy-avermectin B2a/2b aglycone;

13-epi-fluoro-13-deoxy-23-deoxy-23-thioacetyl-24-hydroxy-avermectin B2a/2b aglycone-5-oxime;

23-deoxy-23-thioacetyl-24-hydroxy-avermectin B2a/2b-5-oxime;

24-cyano-avermectin B2a/2b;

4''-epi-acetylamino-4''-deoxy-24-cyano-avermectin B2a/2b;

13-epi-0-acetyl-24-cyano-avermectin B2a/2b aglycone;

13-deoxy-24-cyano-avermectin B2a/2b aglycone;

13-epi-fluoro-13-deoxy-24-cyano-avermectin B2a/2b aglycone;

13-epi-fluoro-13-deoxy-24-cyano-avermectin B2a/2b aglycone-5-oxime; and 24-cyano-avermectin B2a/2b-5-oxime.

DETAILED DESCRIPTION OF A PREFERRED EMBODIMENT

In a preferred embodiment of the instant invention, thiol-derived aluminum sulfides were reacted with avermectin derivative to achieve nucleophilic substitution of an avermectin 23,24-epoxide (the preparation of which is described in: Tetrahedron Letters, 33, 1709–1712, 1992, which is hereby incorporated by reference).

In a particularly preferred embodiment, substitution was accomplished through the use of dialkylaluminum sulfides to achieve a nucleophilic ring opening of the 23,24-expoxide of avermectin $B_{2a}$ (1) under mild reaction conditions.

epoxide 1
R = phenoxyacetyl   R' = TMS

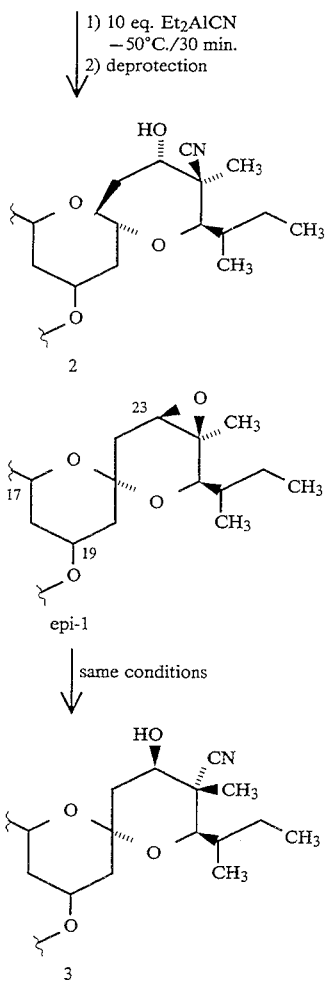
While the low temperature addition of diethylaluminum cyanide to epoxide 1 led to a single isomeric product (2 or 3), the addition of a prepared sample of a variety of dimethylaluminum sulfides led to the formation of a product mixture (4 and 5), resulting from epoxide opening at either $C_{23}$ or $C_{24}$ as shown below, and as summarized in Table 1.
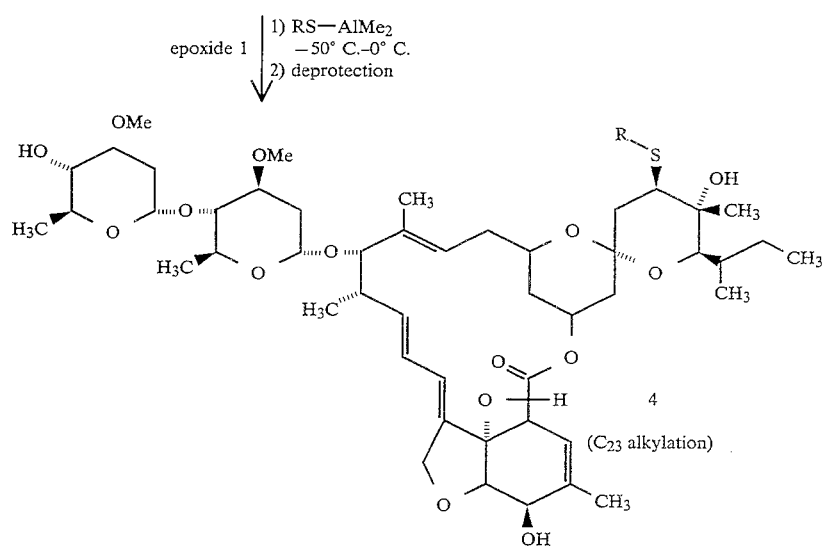

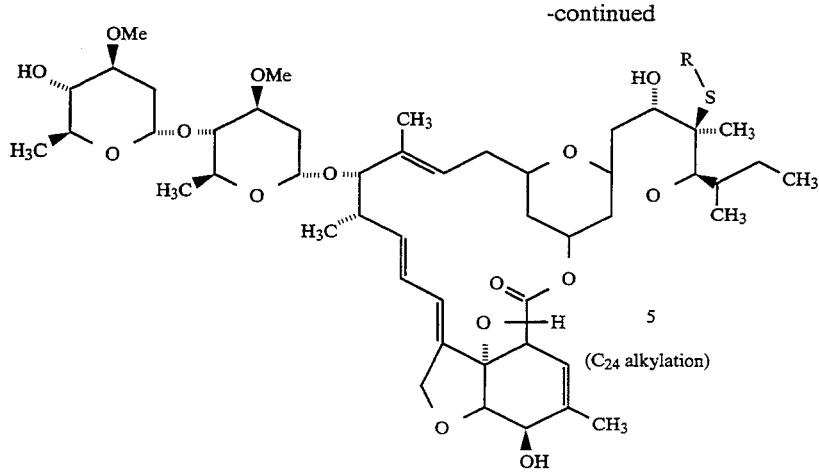

(C24 alkylation)

TABLE 1

| Product | nucleophile | yield | Brine Shrimp assay (ng/mL) |
|---|---|---|---|
| 2 | NC⁻ | 69% | 220 |
| 3 |  | 49% | 430 |
| 4a | 2-pyridyl-S⁻ | 15% | 1300 |
| 5a |  | 12% | 870 |
| 4b | 4-pyridyl-S⁻ | 21% | 3470 |
| 5b |  | 11% | 6930 |
| 4c | phenyl-S⁻ | 17% | 1730 |
| 5c |  | 14% | 870 |
| 4d | thiazolyl-S⁻ | 2% | 870 |
| 5d |  | 23% | 870 |
| 4e | imidazolyl-S⁻ | 6% | 3470 |
| 5e |  | 10% | 10415 |
| 4f | 4-F-phenyl-S⁻ | 39% | 1730 |
| 5f |  | 21% | 870 |
| 4g | CH₃C(O)S⁻ | 8% | 1300 |
| 5g |  | 24% | 430 |

The bioactivities listed in Table 1 were evaluated by the brine shrimp (A. Salina) immobilization assay (see Blizzard, T. A.; Ruby, C. L.; Mrozik, H.; Preiser, F. A.; Fisher, M. H. J. Antibiotics, 1989, 42, 1304). The yields given in Table 1 are the result of the ring-opening reaction and subsequent deprotection steps after final purification by silica gel chromatography. The yields are not optimized. Experimentally, the reactions were monitored by TLC until the complete consumption of starting material was observed. The balance of the material was decomposed or otherwise compromised avermectins even under these mildly acidic conditions deglycosidation was a problem, as some monosaccharide products were observed in nearly all cases.

Synthesis of avermectin derivatives in accordance with the instant invention is further illustrated by the following examples:

EXAMPLE 1

24-(4-fluoro-thiophenyl)-avermectin $B_{2a}/B_{2b}$ and 23-deoxy-23-(4-fluoro-thiophenyl)-24-hydroxy-avermectin $B_{2a}/B_{2b}$ To a −45° C. solution of 4-fluorothiophenol (124 μL, 1.16 mmol) in 25 mL dichloromethane was added trimethylaluminum (580 μL, 2M in hexane, 1.16 mmol) dropwise via syringe. The resulting thioaluminum reagent was allowed to stir for 4 hours while warming to 23° C. The freshly-formed thioaluminum reagent was again cooled to −40° C., and to this solution was added a solution of α-23,24-epoxy-7-trimethylsilyl-ivermectin (112 mg, 0.117 mmol) in 2 mL dichloromethane dropwise via syringe. The reaction mixture was stirred at −40° C. and monitored by TLC until the starting epoxide was completely consumed (approximately 1 hour). The reaction mixture was then diluted with dichloromethane and washed successively with saturated aqueous ammonium chloride and brine, and dried over $MgSO_4$. Filtration and evaporation of the organic phase gave a crude oil which was purified by preparative TLC (3:1 ethyl acetate/hexane, $R_f \sim 0.55$) to provide 110 mg of the desired alkylation products, in approximately a 2:1 ratio of the 23 vs. 24 alkylation products.

This mixture of products was dissolved in 6 mL of a stock THF/HF/pyridine mixture (25 mL:40 mL:20 mL) in a polyethylene bottle and stirred overnight at room temperature. The reaction mixture was poured over ice in a separatory funnel and washed with saturated sodium bicarbonate and brine, and the organic phase evaporated in vacuo. Purification was accomplished by HPLC (80%:20% methanol/water) to yield 25.5 mg of 24-(4-fluoro-thiophenyl)-Avermectin $B_{2a}$ and 46 mg of 23-deoxy-23-(4-fluoro-thiophenyl)-24-hydroxy-Avermectin $B_{2a}$. Each of these structural assignments was based on their NMR and mass spectral properties.

EXAMPLE 2

24-(2-thiopyridyl)-avermectin $B_{2a}/B_{2b}$ and 23-deoxy-23-(2-thiopyridyl)-24hydroxy-avermectin $B_{2a}/B_{2b}$ The procedure used in Example 1 was applied to α-23,24-epoxy-7-trimethylsilyl-ivermectin, substituting 2-thiopyridine in the place of 4-fluorothiophenol for use in preparation of the thioaluminum reagent. This procedure provided the desired 24-(2-thiopyridyl)-Avermectin $B_{2a}$ and 23-(2-thiopyridyl)-24-hydroxy-24-methyl-Avermectin $B_{2a}$ after purification by HPLC (80%:20% methanol/water). Each of these structural isomers was characterized by its NMR and mass spectra.

EXAMPLE 3

24-(4-thiopyridyl)-avermectin $B_{2a}/B_{2b}$ and 23-deoxy-23-(4-thiopyridyl)-24-hydroxy-avermectin $B_{2a}/B_{2b}$ The procedure used in Example 1 was applied to α-23,24-epoxy-7-trimethylsilyl-ivermectin, substituting 4-thiopyridine in the place of 4-fluorothiophenol for use in preparation of the thioaluminum reagent. This procedure provided the desired 24-(4-thiopyridyl)-Avermectin $B_{2a}$ and 23-deoxy-23-(4-thiopyridyl)-24-hydroxy-avermectin $B_{2a}/B_{2b}$ after purification by HPLC (80%:20% methanol/water). Each of these structural isomers was characterized by its NMR and mass spectra.

EXAMPLE 4

24-(2-mercaptothiazolyl)-avermectin $B_{2a}/B_{2b}$ and 23-deoxy-23-(2-mercaptothiazolyl)-24-hydroxy-avermectin $B_{2a}/B_{2b}$ The procedure used in Example 1 was applied to α-23,24-epoxy-7-trimethylsilyl-ivermectin, substituting 2-mercaptothiazoline in the place of 4-fluorothiophenol for use in preparation of the thioaluminum reagent. This procedure provided the desired 24-(2-mercaptothiazolyl)-Avermectin $B_{2a}$ and 23-deoxy-23-(2-mercaptothiazolyl)-24-hydroxy-avermectin $B_{2a}/B_{2b}$ after purification by HPLC (77%:23% methanol/water). Each of these structural isomers was characterized by its NMR and mass spectra.

EXAMPLE 5

24-(2-mercaptoimidazolyl)-avermectin $B_{2a}/B_{2b}$ and 23-deoxy-23-(2-mercaptoimidazolyl)-24-hydroxy-avermectin $B_{2a}/B_{2b}$ The procedure used in Example 1 was applied to α-23,24-epoxy-7-trimethylsilyl-ivermectin, substituting 2-mercaptoimidazole in the place of 4-fluorothiophenol for use in preparation of the thioaluminum reagent. This procedure provided the desired 24-(2-mercaptoimidazolyl)-Avermectin $B_{2a}$ and 23-deoxy-23-(2-mercaptoimidazolyl)-24-hydroxy-avermectin $B_{2a}/B_{2b}$ after purification by column chromatography (75:25 ethyl acetate/hexane). Each of these structural isomers was characterized by its NMR and mass spectra.

EXAMPLE 6

24-thioacetyl-avermectin $B_{2a}/B_{2b}$ and 23-deoxy-23-thioacetyl-24-hydroxy-avermectin $B_{2a}/B_{2b}$ The procedure used in Example 1 was applied to α-23,24-epoxy-7-trimethylsilyl-ivermectin, substituting thioacetic acid in the place of 4-fluorothiophenol for use in preparation of the thioaluminum reagent. This procedure provided the desired 24-thioacetyl-Avermectin $B_{2a}$ and 23-deoxy-23-thioacetyl-24-hydroxy-avermectin $B_{2a}/B_{2b}$ after purification by column chromatography (75:25 ethyl acetate/hexane). Each of these structural isomers was characterized by its NMR and mass spectra.

EXAMPLE 7

24-a-cyano-avermectin $B_{2a}/B_{2b}$

To a −50° C. solution of β-23,24-epoxy-7-trimethylsilyl-ivermectin (93 mg, 0.097 mmol) in 5 mL dichloromethane was added dropwise via syringe 0.97 mL diethylaluminum cyanide (1.0M). The reaction mixture was stirred from −50° C. to −10° C. and monitored by TLC until the starting epoxide was completely consumed (approximately 2 hours). The reaction mixture was then diluted with dichloromethane and washed successively with saturated aqueous ammonium chloride and brine, and dried over MgSO$_4$. Filtration and evaporation of the organic phase gave a crude oil which was dissolved in 6 mL of a stock THF/HF/pyridine mixture (25 mL:40 mL:20 mL) in a polyethylene bottle and stirred overnight at room temperature. The reaction mixture was poured over ice in a separatory funnel and washed with saturated sodium bicarbonate and brine, and the organic phase evaporated in vacuo. Purification was accomplished by PTLC (75:25 ethyl acetate/hexane) to yield 61.1 mg of the title compound characterized by its NMR and mass spectra.

EXAMPLE 8

4″, 5-Di-0-phenoxyacetyl-avermectin $B_{2a}/B_{2b}$

To a solution of 3 g of avermectin $B_{2a}/B_{2b}$ in 30 mL dichloromethane and 0.85 mL of pyridine at 0° C. is added dropwise a solution of 1.41 mL of phenoxyacetyl chloride in 30 mL of dichloromethane. After the addition was completed, the reaction mixture was stirred at 20° C. for one hour. The mixture was then added to 75 mL of ice-water and extracted with ether. The combined extracts were dried (MgSO$_4$) and evaporated to yield the desired products. Chromatographic separation on silica gel affords the title compounds characterized by their NMR and Mass Spectral data.

EXAMPLE 9

4″, 5-Di-0-phenoxyacetyl-7,23-di-0-trimethylsilyl-avermectin $B_{2a}/B_{2b}$

To 3.1 g of 4″, 5-Di-0-phenoxyacetyl-avermectin $B_{2a}/B_{2b}$ in 10 mL of DMF was added 20 mL of BSTFA. The mixture was stirred for 24 hours at room temperature before the solvent and excess BSTFA were removed in vacuo. Flash chromatographic purification on silica gel gives the title compounds characterized by their NMR and Mass Spectral data.

EXAMPLE 10

4″, 5-Di-0-phenoxyacetyl-7-0-trimethylsilyl-avermectin $B_{2a}/B_{2b}$

To a solution of 3.3g of 4″,5-Di-0-phenoxyacetyl-7,23-di-0-trimethylsilyl-avermectin $B_{2a}/B_{2b}$ in 270 mL of THF was added 30 mL of water and 30 mL of acetic acid. The mixture was stirred at room temperature for 48 hours before the THF was removed in vacuo. The acetic acid was neutralized by the addition of aqueous sodium bicarbonate solution and the product was extracted with ethyl acetate. The product obtained after evaporation of the solvent was purified by column chromatography and characterized by NMR and mass spectroscopy.

EXAMPLE 11

4",5-Di-0-phenoxyacetyl-7-0-trimethylsilyl-22-hydro-24-dehydro-avermectin $B_{1a}/B_{1b}$ To a solution of 304 mg of 4", 5-Di-0-phenoxy-acetyl-7-0-trimethylsilyl-avermectin $B_{2a}/B_{2b}$ in 2.5 mL of dichloromethane was added 70 μL of DAST. After 12 minutes the mixture was eluted on three 1000 μm thick silica gel plates with 33% ethyl acetate/hexane. The major band, $R_f$=0.5, was removed and extracted to afford the titled compound characterized by NMR and mass spectroscopy.

EXAMPLE 12

5-0-phenoxyacetyl-22-hydro-24-dehydro-avermectin $B_{1a}/B_{1b}$ aglycone

4",5-Di-0-phenoxyacetyl-7-0-trimethylsilyl-22-hydro-24-dehydro-avermectin $B_{1a}/B_{1b}$ (3 g, 2.47 mmol) is added to a solution of 1% $H_2SO_4$ in methanol and is stirred for 18° C. for 16 hours under nitrogen. Chloroform is added and the solution is washed with aqueous sodium bicarbonate and water, and the organic extracts are concentrated in vacuo. The title compound is obtained after purification by column chromatography and is characterized by NMR and mass spectroscopy.

EXAMPLE 13

5-0-phenoxyacetyl-22-hydro-24-dehydro-13-deoxy-13-chloro-avermectin $B_{1a}/B_{1b}$ aglycone To a solution of 2 g (1.82 mmol) of 5-0-phenoxyacetyl-22-hydro-24-dehydro-avermectin $B_{1a}/B_{1b}$ aglycone is added a solution of 2-nitrobenzenesulfonyl chloride (2.01 g, 9.08 mmol), DMAP (1.33 g, 10.90 mmol), and diisopropylethylamine (1.89 mL, 10.90 mmol) in dichloromethane at 18° C. and is stirred for 2 hours. The organic mixture is extracted with brine and concentrated in vacuo, giving the title compound after purification by silica gel chromatography (ethyl acetate/hexane), as characterized by its NMR and mass spectra.

EXAMPLE 14

5-0-phenoxyacetyl-22-hydro-24-dehydro-13-deoxy-avermectin B1a/B1b aglycone

A solution of 1.5 g (1.38 mmol) of 5-0-phenoxyacetyl-22-hydro-24-dehydro-13-deoxy-13-chloro-avermectin $B_{1a}/B_{1b}$ aglycone is treated with 3.72 mL (13.82 mmol) of tri-n-butyltin hydride in toluene for 2 hours at 85° C. in the presence of a catalytic amount of AIBN. Concentration and purification of the crude residue provides the title compound as characterized by its NMR and mass spectra.

EXAMPLE 15

5-0-phenoxyacetyl-22-hydro-24-dehydro-23,24-oxy-13-deoxy-avermectin $B_{1a}/B_{1b}$ aglycone To a solution of 1 g (0,922 mmol) of 5-0-phenoxyacetyl-22-hydro-24-dehydro-13-deoxy-avermectin $B_{1a}/B_{1b}$ aglycone in 10 mL of dichloromethane is added a solution of 80% mCPBA (238 mg, 1.106 mmol) in dichloromethane. After 30 minutes, 300 mg of dimethyl sulfide is added and the reaction mixture is stirred another 30 minutes to consume any remaining mCPBA. The mixture is then concentrated in vacuo and the residue is dissolved in ether and washed successively with aqueous sodium bicarbonate and brine. The ether is removed and the residue is flash chromatographed to afford the title epoxy compound, characterized by its $^1$H-NMR and mass spectra.

EXAMPLE 16

5-0-t-butyldimethylsilyl-22-hydro-24-dehydro-avermectin $B_{1a}/B_{1b}$

A solution of 50 g (57.3 mmol) of dried 22-hydro-24-dehydro-avermectin $B_{1a}/B_{1b}$, 8.57 g (126.1 mmol) of imidazole and 8.64 g (57.3 mmol) of tert-butyldimethylsilyl chloride in 400 mL of anhydrous dimethylformamide is stirred at room temperature for 50 minutes. The reaction mixture is poured into 1.5 L of ice cold water and the aqueous phase is extracted four times with 200 mL of ether. The organic phase is washed twice with water, aqueous sodium chloride solution, dried with magnesium sulfate and concentrated in vacuo to a white foam. The crude product is purified by silica gel chromatography with a methylene chloride-ethyl acetate-90:10 to 70:30 solvent system to give 5-0-t-butyldimethylsilyl-22-hydro-24-avermectin $B_{1a}/B_{1b}$ as an amorphous foam, which is characterized by its $^1$H-NMR and mass spectra.

EXAMPLE 17

5-0-t-butyldimethylsilyl-4"-oxo-22-hydro-24-dehydro-avermectin $B_{1a}/B_{1b}$

To a solution containing 9.1 mL (0.103 mmol) of oxalyl chloride in 230 mL of dry methylene chloride stirred at −60° C. is added 15 mL (0.211 mmol) of dry dimethylsulfoxide dissolved in 120 mL of dry methylene chloride during 15 minutes. Then a solution of 50.6 g of 5-0-t-butyldimethylsilyl-22-hydro-24-dehydro-avermectin $B_{1a}/B_{1b}$ dissolved in 230 mL of dry methylene chloride is added over a period of 15 minutes while maintaining the temperature at −60° C. The reaction mixture is stirred at this temperature for 30 minutes when 65 mL of dry triethylamine is added. The mixture is stirred for 5 additional minutes at −60° C., and then the cooling bath is removed and the reaction mixture is allowed to come to ambient temperature. After addition of water the reaction product is extracted with methylene chloride, the extract is washed with water, dried and concentrated in vacuo to a yellow foam. This product is identified by its 1H-NMR and mass spectra as 5-0-t-butyldimethylsilyl-4"-oxo-22-hydro-24-dehydro-avermectin $B_{1a}/B_{1b}$, which is used for further chemical reactions without purification.

EXAMPLE 18

4"-epi-amino-4"-deoxy-5-0-t-butyldimethylsilyl-22-hydro-24-dehydro-avermectin $B_{1a}/B_{1b}$ For the reductive amination 15.3 mg (0.244 mmol) of sodium cyanoborohydride is added to a solution of 200 mg (0.203 mmol) of 5-0-t-butyldimethylsilyl-4"-oxo-22-hydro-24-dehydro-avermectin $B_{1a}/B_{1b}$ (from Example 17) and 160 mg of ammonium acetate in 3 mL of methanol, and the reaction mixture is stirred at room temperature for 1 hour. Then the solution is poured into aqueous sodium carbonate and the organic products are extracted with ethyl acetate. The extract is washed with water, dried, and concentrate in vacuo to a yellow oil. Preparative silica gel chromatography with a 98:2 methylene chloride:methanol solvent system gives 4''-epi-amino-5-0-t-butyldimethylsilyl-22-hydro-24-dehydro-avermectin $B_{1a}/B_{1b}$ and 4''-amino-4''-deoxy-5-0-t-butyldimethylsilyl-22-hydro-24-dehydro-avermectin $B_{1a}/B_{1b}$ as light colored foams, which are characterized by their $^1$H-NMR and mass spectral data.

EXAMPLE 19

4''-epi-amino-4''-deoxy-5-0-t-butyldimethylsilyl-22-hydro-24-dehydro-23,24-oxy-avermectin $B_{1a}/B_{1b}$ To a solution of 1.2 g (1.22 mmol) of 4''-epi-amino-4''-deoxy-5-0-t-butyldimethylsilyl-22-hydro-24-dehydro-avermectin $B_{1a}/B_{1b}$ in 10 mL of dichloromethane is added a solution of 316 mg (1.46 mmol) of 80% mCPBA in dichloromethane. After 30 minutes 300 mg of dimethyl sulfide is added and the reaction mixture is stirred an additional 30 minutes. The reaction mixture is then concentrated in vacuo and the residue is dissolved in ether and washed successively with aqueous sodium bicarbonate and brine. The ether is removed and the solid residue is purified by flash chromatography to afford 4''-epi-amino-4''-deoxy-5-0-t-butyldimethylsilyl-22-hydro-24-dehydro-α-23,24-oxy-avermectin $B_{1a}/B_{1b}$ and 4''-epi-amino-4''-deoxy-5-0-t-butyldimethyl-silyl-22-hydro-24-dehydro-β-23,24-oxy-avermectin $B_{1a}/B_{1b}$, as characterized by their $^1$H-NMR and mass spectral data.

EXAMPLE 20

4''-epi-amino-4''-deoxy-24-thiophenyl-avermectin $B_{2a}/B_{2b}$ and
4''-epi-amino-4''-deoxy-23-deoxy-23-thiophenyl-24-hydroxy-avermectin $B_{2a}/B_{2b}$ To a −45° C. solution of thiophenol (124 μL, 1.16 mmol) in 25 mL dichloromethane is added trimethylaluminum (580 μL, 2M in hexane, 1.16 mmol) dropwise via syringe. The resulting thioaluminum reagent is allowed to stir for 4 hours while warming to 23° C. The freshly formed thioaluminum reagent is again cooled to −40° C., and to this solution is added a solution of 4''-epi-amino-4''-deoxy-5-0-t-butyl dimethyl-silyl-22-hydro-24-dehydro-α-23,24-oxy-avermectin $B_{1a}/B_{1b}$ (116 mg, 0.116 mmol) in 2 mL dichloromethane dropwise via syringe. The reaction mixture is stirred at −40° C. and monitored by TLC until the starting epoxide is completely consumed (approximately 1 hour). The reaction mixture is then diluted with dichloromethane and washed successively with saturated aqueous ammonium chloride and brine, and dried over MgSO$_4$. Filtration and evaporation of the organic phase gives a crude oil which is purified by preparative TLC (3:1 ethyl acetate/hexane, R$_f$~0.55) to provide a mixture of the desired alkylation products.

This mixture of products is dissolved in 6 mL of a stock THF/HF/pyridine mixture (25 mL:40 mL:20 mL) in a polyethylene bottle and stirred overnight at room temperature. The reaction mixture is poured over ice in a separatory funnel and washed with saturated sodium bicarbonate and brine, and the organic phase evaporated in vacuo. Purification is accomplished by HPLC (80%:20% methanol/water) to yield the desired 4''-epi-amino-4''-deoxy-24-thiophenyl-avermectin $B_{2a}/B_{2b}$ and 4''-epi-amino-4''-deoxy-23-deoxy-23-thiophenyl-24-hydroxy-avermectin $B_{2a}/B_{2b}$, as characterized by their NMR and mass spectral properties.

EXAMPLE 21

4''-epi-Acetylamino-4''-deoxy-24-thiophenyl-avermectin $B_{2a}/B_{2b}$ and
4''-epi-Acetylamino-4''-deoxy-23-thiophenyl-24-hydroxy-24-methyl-avermectin $B_{2a}/B_{2b}$ A solution of 50 mg (50.3 mmol) of 4''-epi-Acetylamino-4''-deoxy-24-thiophenyl-avermectin $B_{2a}/B_{2b}$ and 4''-epi-Acetylamino-4''-deoxy-23-deoxy-23-thiophenyl-24-hydroxy-avermectin $B_{2a}/B_{2b}$ in 0.5 mL of methylene chloride is treated with 7.1 μL (75.4 mmol) of acetic anhydride at room temperature for 1 hour. The reaction mixture is then diluted with ethyl acetate and washed with dilute sodium bicarbonate and water, and is dried and concentrated in vacuo to a white foam, which is characterized by its $^1$H-NMR and mass spectrum as the title compounds.

EXAMPLE 22

22-hydro-24-dehydro-Avermectin $B_{1a}/B_{1b}$ monosaccharide and aglycone

A solution of 4.6 mL of water, 4.6 mL of concentrated sulfuric acid, and 17 mL of tetrahydrofuran is added over 30 minutes to a solution of 2.22 g (2.54 mmol) of dried 22-hydro-24-dehydro-avermectin $B_{1a}/B_{1b}$ in 20 mL of THF stirred in an ice bath. Then the reaction mixture is stirred 24 hours at room temperature. Addition of ice water, extraction with methylene chloride, washing with aqueous sodium bicarbonate solution and water, drying and concentration in vacuo gives a brown foam. Purification and separation by silica gel chromatography using methylene chloride/ethyl acetate solvent mixtures affords pure 22-hydro-24-dehydro-Avermectin $B_{1a}/B_{1b}$ monosaccharide and 22-hydro-24-dehydro-Avermectin $B_{1a}/B_{1b}$ aglycone, as characterized by their NMR and mass spectral properties.

EXAMPLE 23

4',5-Di-0-t-butyldimethylsilyl-22-hydro-24-dehydro-avermectin $B_{1a}/B_{1b}$ monosaccharide and
5-0-t-butyldimethylsilyl-22-hydro-24-dehydro-avermectin $B_{1a}/B_{1b}$ monosaccharide To a solution of 58.2 g (79.8 mmol) of dried 22-hydro-24-dehydro-avermectin $B_{1a}/B_{1b}$ monosaccharide in 400 mL of sieve-dried DMF and 30 mL of freshly distilled triethylamine is added a solution of 36.1 g (239.5 mmol, 3 eq.) of t-butyldimethylsilyl chloride in 200 mL of dichloromethane. The mixture is stirred at room temperature for 16 hours and then poured into ice water and extracted with dichloromethane. The organic phases are combined and washed with water, brine, and dried over magnesium sulfate. Evaporation of the solvent affords and oil which is purified by silica gel HPLC using 20% ethyl acetate/hexane to yield the title compounds, as characterized by their NMR and mass spectral properties.

EXAMPLE 24

4,,5-Di-0-t-butyldimethylsilyl-22-hydro-24-dehydro-23,24-oxy-avermectin $B_{1a}/B_{1b}$ monosaccharide To a solution of 1.2 g (1.25 mmol) of 4',5-Di-0-t-butyldimethylsilyl-22-hydro-24-dehydro-avermectin $B_{1a}/B_{1b}$ monosaccharide in 10 mL of dichloromethane is added a solution of 324 mg (1.50 mmol) of 80% mCPBA in dichloromethane. After 30 minutes 300 mg of dimethyl sulfide is added and the reaction mixture is stirred an additional 30 minutes. The reaction mixture is then concentrated in vacuo and the residue is dissolved in ether and washed successively with aqueous sodium bicarbonate and brine. The ether is removed and the solid residue is purified by flash chromatography to afford 4',5-Di-0-t-butyldimethylsilyl-22-hydro-24-dehydro-α-23,24-oxy-avermectin $B_{1a}/B_{1b}$ monosaccharide and 4',5-Di-0-t-butyldimethylsilyl-22-hydro-24-dehydro-β-23,24-oxyavermectin $B_{1a}/B_{1b}$ monosaccharide, as characterized by their $^1$H-NMR and mass spectral data.

EXAMPLE 25

24-(2-mercaptopyridyl)-avermectin $B_{2a}/B_{2b}$ monosaccharide and
23-deoxy-23-(2-mercaptopyridyl)-24-hydroxy-avermectin $B_{2a}/B_{2b}$ monosaccharide The procedure used in Example 20 is applied to 4',5-Di-0-t-butyldimethylsilyl-22-hydro-24-dehydro-23,24-α-oxyavermectin $B_{1a}/B_{1b}$ monosaccharide, substituting 2-mercartopyridine in the place of thiophenol for use in preparation of the thioaluminum reagent. This procedure provides the desired 24-(2-thio-pyridyl)-avermectin $B_{2a}/B_{2b}$ monosaccharide and 23-deoxy-23-(2-mercartopyridyl)-24-hydroxy-avermectin $B_{2a}/B_{2b}$ monosaccharide after purification by HPLC (80%:20% methanol/water). Each of these structural isomers is characterized by its NMR and mass spectra.

EXAMPLE 26

13,5-Di-0-t-butyldimethylsilyl-22-hydro-24-dehydroavermectin $B_{1a}/B_{1b}$ aglycone and
5-0-t-butyldimethylsilyl-22-hydro-24-dehydroavermectin $B_{1a}/B_{1b}$ aglycone To a solution of 40.0 g (68.4 mmol) of dried 24-dehydroavermectin $B_{1a}/B_{1b}$ aglycone in 400 mL of sieve-dried DMF and 30 mL of freshly distilled triethylamine is added a solution of 30.9 g (205 mmol, 3 eq.) of t-butyldimethylsilyl chloride in 200 mL of dichloromethane. The mixture is stirred at room temperature for 16 hours and then poured into ice water and extracted with dichloromethane. The organic phases are combined and washed with water, brine, and dried over magnesium sulfate. Evaporation of the solvent affords and oil which is purified by silica gel HPLC using 20% ethyl acetate/hexane to yield the title compounds, as characterized by their NMR and mass spectral properties.

EXAMPLE 27

13,5-Di-0-t-butyldimethylsilyl-22-hydro-24-dehydro-23,24-oxy-avermectin $B_{1a}/B_{1b}$ aglycone To a solution of 1.2 g (1.48 mmol) of 13,5-Di-0-t-butyldimethylsilyl-22-hydro-24-dehydro-avermectin $B_{1a}/B_{1b}$ aglycone in 10 mL of dichloromethane is added a solution of 382 mg (1.77 mmol) of 80% mCPBA in dichloromethane. After 30 minutes 300 mg of dimethyl sulfide is added and the reaction mixture is stirred an additional 30 minutes. The reaction mixture is then concentrated in vacuo and the residue is dissolved in ether and washed successively with aqueous sodium bicarbonate and brine. The ether is removed and the solid residue is purified by flash chromatography to afford 13,5-Di-0-t-butyldimethylsilyl-22-hydro-24-dehydro-α-23,24-oxyavermectin $B_{1a}/B_{1b}$ aglycone and 13,5-Di-0-t-butyldimethylsilyl-22-hydro-24-dehydro-B-23,24-oxyavermectin $B_{1a}/B_{1b}$ aglycone, as characterized by their $^1$H-NMR and mass spectral data.

EXAMPLE 28

24-(2-mercaptothiazolyl)-avermectin $B_{2a}/B_{2b}$ aglycone and
23-deoxy-23-(2-mercaptothiazolyl)-24-hydroxy-avermectin $B_{2a}/B_{2b}$ aglycone The procedure used in Example 20 is applied to 13,5-Di-0-t-butyldimethylsilyl-22-hydro-24-dehydro-α-23,24-oxyavermectin $B_{1a}/B_{1b}$ aglycone, substituting 2-mercaptothiazole in the place of thiophenol for use in preparation of the thioaluminum reagent. This procedure provides the desired 24-(2-mercapto-thiazolyl)-avermectin $B_{2a}/B_{2b}$ aglycone and 23-(2-mercaptothiazolyl)-24-hydroxy-avermectin $B_{2a}/B_{2b}$ aglycone after purification by HPLC (80%:20% methanol/water). Each of these structural isomers is characterized by its NMR and mass spectra.

EXAMPLE 29

5-0-tert-Butyldimethylsilyl-13-deoxy-13-fluoro-22-hydro-24-dehydro-avermectin $B_{1a}/B_{1b}$ aglycone A solution of 0.4 mL (3.02 mmol) of diethylaminosulfur trifluoride in 8 mL of dichloromethane is stirred at −65° C. under $N_2$. To this is added dropwise a solution of 2 g (2.86 mmol) of 5-0-tert-Butyldimethylsilyl-22-hydro-24-dehydro-avermectin $B_{1a}/B_{1b}$ aglycone in 8 mL of dichloromethane during 15 minutes. The reaction mixture is stirred at −65° C. for 1 hour, at −20° C. for 30 minutes, and then warmed to room temperature and stirred for 1.5 hours. The reaction mixture is then poured into dilute aqueous $NaHCO_3$ solution, extracted with dichloromethane, washed with water, dried, and concentrated in vacuo to a light glass. Purification by preparative thin layer chromatography with hexane/ethyl acetate solvent mixtures gives a mixture of 5-0-tert-Butyldimethyl-silyl-13-deoxy-13α-fluoro-and 13-deoxy-13β-fluoro-22-hydro-24-dehydro-avermectin $B_{1a}/B_{1b}$ aglycones, which are characterized by their NMR and mass spectra.

EXAMPLE 30

5-0-tert-Butyldimethylsilyl-13-deoxy-13-fluoro-22-hydro-24-dehydro-23,24-oxyavermectin $B_{1a}/B_{1b}$ aglycone To a solution of 1.2 g (1.71 mmol) of 5-0-tert-Butyldimethylsilyl-13-deoxy-13-fluoro-22-hydro-24-dehydro-avermectin $B_{1a}/B_{1b}$ aglycone in 10 mL of dichloromethane is added a solution of 443 mg (2.05 mmol) of 80% mCPBA in dichloromethane. After 30 minutes 500 mg of dimethyl sulfide is added and the reaction mixture is stirred an additional 30 minutes. The reaction mixture is then concentrated in vacuo and the residue is dissolved in ether and washed successively with aqueous sodium bicarbonate and brine. The ether is removed and the solid residue is purified by flash chromatography to afford 5-0-tert-Butyldimethylsilyl-13-deoxy-13-fluoro-22-hydro-24-dehydro-α-23,24-oxyavermectin $B_{1a}/B_{1b}$ aglycone and 5-0-tert-Butyldimethylsilyl-13-deoxy-13-fluoro-22-hydro-24-dehydro-β-23,24-oxyavermectin $B_{1a}/B_{1b}$ aglycone, as characterized by their $^1$H-NMR and mass spectral data.

EXAMPLE 31

13-deoxy-13-fluoro-24-(2-mercaptoimidazolyl)-avermectin $B_{2a}/B_{2b}$ aglycone and 13-deoxy-13-fluoro-23-deoxy-23-(2-mercaptoimidazolyl)-24-hydroxy-avermectin $B_{2a}/B_{2b}$ aglycone The procedure used in Example 20 is applied to 5-0-tert-Butyldimethylsilyl-13-deoxy-13-fluoro-22-hydro-24-dehydro-α-23,24-oxyavermectin $B_{1a}/B_{1b}$ aglycone, substituting 2-mercaptoimidazole in the place of thiophenol for use in preparation of the thioaluminum reagent. This procedure provides the desired 13-deoxy-13-fluoro-24-(2-mercaptoimidazolyl)-avermectin $B_{2a}/B_{2b}$ aglycone and 13-deoxy-13-fluoro-23-deoxy-23-(2-mercaptoimidazolyl)-24-hydroxy-avermectin $B_{2a}/B_{2b}$ aglycone after purification by HPLC (80%:20% methanol/water). Each of these structural isomers is characterized by its NMR and mass spectra.

EXAMPLE 32

4''-0-t-Butyldimethylsilyl-7-0-trimethylsilyl-22-hydro-24-dehydro-oxyavermectin $B_{1a}/B_{1b}$-5-ketoxime To a solution of 170 mg (0.158 mmol) of 4''-0-t-Butyldimethylsilyl-7-0-trimethylsilyl-22-hydro-24-dehydro-oxyavermectin $B_{1a}/B_{1b}$ in 3 mL of dry DMF is added at room temperature 59.6 mg (0.158 mmol) of 98% pyridinium dichromate. After 1.5 hours at room temperature, 5 mL of water and 5 mL of ethyl acetate are added. The resulting mixture is poured into a separatory funnel containing 30 mL of water and extracted with water. The organic layers are combined and dried over sodium sulfate, filtered and concentrated in vacuo to provide the corresponding ketone that is used without further purification.

To a solution of 866 mg (0.817 mmol) of 4''-0-t-Butyldimethylsilyl-7-0-trimethylsilyl-5-oxo-22-hydro-24-dehydro-23,24-oxyavermectin $B_{1a}/B_{1b}$ in 5 mL of dry ethyl acetate is added 817 μL (817 μmol, 1M in diethyl ether) of zinc chloride followed by 86 mg (0.817 mmol) of 0-(trimethylsilyl)hydroxylamine at room temperature. The reaction mixture is stirred at room temperature for 2 hours, then quenched by the addition of 10 mL of saturated aqueous sodium bicarbonate. The reaction mixture is extracted with ethyl acetate and the combined organic layers are dried over sodium sulfate, filtered and concentrated. The crude silyl oxime-ether is then dissolved in 8 mL of dry methanol. The solution is cooled to 0° C. and 3 mL of 1% p-toluenesulfonic acid in methanol is added dropwise. The reaction is quenched after 1 hour by addition of 10 mL of saturated aqueous sodium bicarbonate. The mixture is washed with water and extracted into dichloromethane. The organic layer is dried over sodium sulfate and filtered and concentrated to provide the crude product. Purification by preparative TLC yields the desired 4''-0-t-Butyldimethylsilyl-7-0-trimethylsilyl-22-hydro-24-dehydro-23,24-oxyavermectin $B_{1a}/B_{1b}$-5-ketoxime.

EXAMPLE 33

24-thioacetyl-avermectin $B_{2a}/B_{2b}$-5-ketoxime and 23-deoxy-23-thioacetyl-24-hydroxy-avermectin $B_{2a}/B_{2b}$-5-ketoxime The procedure used in Example 1 was applied to 4''-0-t-Butyldimethylsilyl-7-0-trimethylsilyl-22-hydro-24-dehydro-oxyavermectin $B_{1a}/B_{1b}$-5-ketoxime, substituting thioacetic acid in the place of 4-fluorothiophenol for use in preparation of the thioaluminum reagent. This procedure provided the desired 24-thioacetyl-avermectin $B_{2a}/B_{2b}$-5-ketoxime and 23-deoxy-23-thioacetyl-24-hydroxy-avermectin $B_{2a}/B_{2b}$-5-ketoxime after purification by column chromatography (75:25 ethyl acetate/hexane). Each of these structural isomers is characterized by its NMR and mass spectra.

EXAMPLE 34

5-0-t-butyldimethylsilyl-4''-0-(2-(Methoxyethoxy)-methyl)-22-hydro-24-dehydro-avermectin $B_{1a}/B_{1b}$ 2-(Methoxyethoxy)methyl chloride (360 μL, 3.15 mmol) is added dropwise at room temperature to a stirring solution containing 200 mg (0.203 mmol) of 5-0-t-butyldimethylsilyl-22-hydro-24-dehydro-avermectin $B_{1a}/B_{1b}$ and 650 μL (3.73 mmol) of N,N-diisopropyl-ethylamine in 0.8 mL of methylene chloride under $N_2$. After 20 hours the reaction mixture is diluted with methylene chloride, washed with water, dried and concentrated in vacuo to a light glass. Purification by preparative TLC using methylene chloride containing 0.5 to 5% of methanol as solvent provides 5-0-t-butyldimethylsilyl-4''-0-(2-(Methoxyethoxy)-methyl)-22-hydro-24-dehydro-avermectin $B_{1a}/B_{1b}$, which is characterized by its NMR and mass spectra.

EXAMPLE 35

5-0-t-butyldimethylsilyl-13-0-(2-(Methoxyethoxy)-methyl)-22-hydro-24-dehydro-avermectin $B_{1a}/B_{1b}$ aglycone The procedure employed in Example 34 is followed with 5-0-t-butyldimethylsilyl-22-hydro-24-dehydro-avermectin $B_{1a}/B_{1b}$ aglycone to provide 5-0-t-butyldimethylsilyl-13-0-(2-(Methoxyethoxy)-methyl)-22-hydro-24-dehydro-avermectin $B_{1a}/B_{1b}$ aglycone, which is characterized by its NMR and mass spectra.

EXAMPLE 36

13-0-(2-(Methoxyethoxy)methyl)-24-(2-mercaptothiazolyl)-avermectin $B_{2a}/B_{2b}$ aglycone and 13-0-(2-(Methoxyethoxy)methyl)-23-deoxy-23-(2-mercaptothiazolyl)-24-hydroxy-avermectin $B_{2a}/B_{2b}$ aglycone The procedure used in Example 1 was applied to 5-0-t-butyldimethylsilyl-13-0-(2-(Methoxyethoxy)-methyl)-22-hydro-24-dehydro-α-23,24-oxyavermectin $B_{1a}/B_{1b}$ aglycone, substituting 2-mercaptothiazoline in the place of 4-fluorothiophenol for use in preparation of the thioaluminum reagent. This procedure provided the desired 13-0-(2-(Methoxyethoxy)methyl)-24-(4-thiopyridyl)-avermectin $B_{2a}/B_{2b}$ aglycone and 13-0-(2-(Methoxyethoxy)methyl)-23-deoxy-(4-thio-pyridyl)-24-hydroxy-avermectin $B_{2a}/B_{2b}$ aglycone after purification by HPLC (80%:20% methanol/water). Each of these structural isomers is characterized by its NMR and mass spectra.

What is claimed is:

1. A compound having the following structural formula:

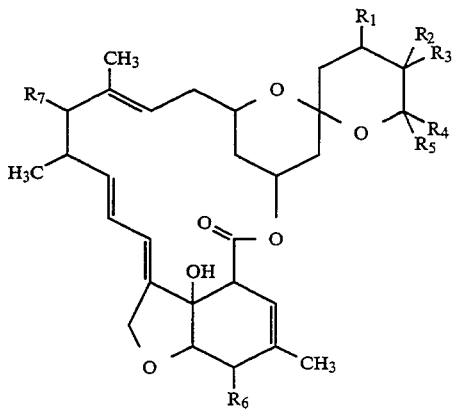
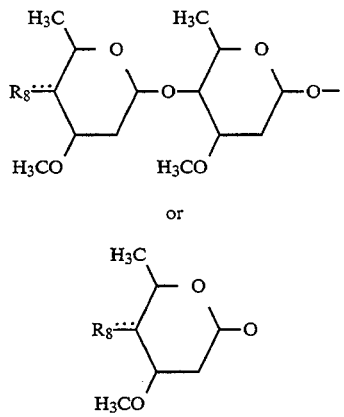

where
R₁ is selected from the group consisting of hydrogen, hydroxy, oxo, thiophenyl, thiophenyl substituted with halogen, thiopyridyl, thiothiazolyl, thioimidazolyl, thioacetyl, and their sulfoxide and sulfone oxidation products;

R₂ is selected from the group consisting of hydrogen, hydroxy, thiophenyl, thiophenyl substituted with halogen, cyano, thiopyridyl, thiothiazolyl, thioimidazolyl, thioacetyl, and their sulfoxide and sulfone oxidation products provided that when R₂ is hydrogen, R₁ is other than hydrogen, hydroxy or oxo;

R₃ is methyl;

R₄ is H isopropyl or sec-butyl;

R₅ is H;

R₆ is OH, oxo, or NOH;

R₇ is H, OH, fluoro, chloro, OCH₂OCH₂CH₂OCH₃, where
R₈ is connected to the 4' or 4" carbon atoms by a single bond and is hydroxy, lower alkanoyloxy, lower alkoxy, amino, N-lower alkyl-amino, N,N-diloweralkylamino, N-loweralkanoylamino, N-lower alkyl-N-lower alkanoylamino, N-loweralkyl silyloxy or phenoxylower-alkanoyloxy, or R₈ is attached to the 4' or 4" carbon atoms by a double bond and is oxo, semicarbazano, N-lower-alkyl-semicarbazano, N,N-diloweralkanoylamino, loweralkanoyhydrazono or loweralkylbenzoylhydrazono.

2. An anthelmintic insecticidal and acaricidal composition comprising an inert carrier and an effective amount of a compound of claim 1.

3. A method of controlling insects in an area infested with parasites comprising applying an effective amount of a compound of claim 1 to the area infested with insects or to the insects infesting the area.

4. A method of controlling parasites in an animal host infested with parasites comprising administering to the animal an effective amount of a compound of claim 1.

* * * * *